US010213375B2

(12) United States Patent
Bacqueville et al.

(10) Patent No.: US 10,213,375 B2
(45) Date of Patent: Feb. 26, 2019

(54) COSMETIC OR DERMATOLOGICAL COMPOSITIONS COMBINING COSMETIQUES RETINALDEHYDE AND GLYCYLGLYCINE OLEAMIDE AND THE COSMETIC OR DERMATOLOGICAL USES THEREOF (71) Applicant: PIERRE FABRE DERMO-COSMETIQUE, Boulogne-Billancourt (FR)

(72) Inventors: Daniel Bacqueville, Toulouse (FR); Patrick Bogdanowicz, Balma (FR); Jean-Hilaire Saurat, Geneva (CH); Olivier Sorg, Geneva (CH)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days.

(21) Appl. No.: 14/895,429

(22) PCT Filed: Jun. 3, 2014

(86) PCT No.: PCT/EP2014/061488
§ 371 (c)(1),
(2) Date: Dec. 2, 2015

(87) PCT Pub. No.: WO2014/195315
PCT Pub. Date: Dec. 11, 2014

(65) Prior Publication Data
US 2016/0206542 A1   Jul. 21, 2016

(30) Foreign Application Priority Data
Jun. 3, 2013 (FR) ...................... 13 55036

(51) Int. Cl.
| A61K 8/64 | (2006.01) |
| A61Q 19/08 | (2006.01) |
| A61Q 19/00 | (2006.01) |
| A61K 38/05 | (2006.01) |
| A61K 31/7048 | (2006.01) |
| A61K 8/67 | (2006.01) |
| A61K 31/11 | (2006.01) |
| A61P 35/00 | (2006.01) |
| A61P 17/00 | (2006.01) |

(52) U.S. Cl.
CPC ............... *A61K 8/64* (2013.01); *A61K 8/671* (2013.01); *A61K 8/678* (2013.01); *A61K 31/11* (2013.01); *A61K 31/7048* (2013.01); *A61K 38/05* (2013.01); *A61P 17/00* (2018.01); *A61P 35/00* (2018.01); *A61Q 19/004* (2013.01); *A61Q 19/08* (2013.01)

(58) Field of Classification Search
None
See application file for complete search history.

(56) References Cited

U.S. PATENT DOCUMENTS 4,732,690 A   3/1988 Shaw
6,569,906 B1 *  5/2003 Redoules ............... A61K 8/602
                                                                514/451

FOREIGN PATENT DOCUMENTS

JP   59-84994 A   5/1984
WO   WO 99/46273 A1   9/1999
WO   WO 99/48470 A1   9/1999

OTHER PUBLICATIONS

YstheAL Anti-wrinkle cream Avene (available Jun. 17, 2010).*
Saurat ("Skin, Sun, and Vitamin A: From Aging to Cancer" The Journal of Dermatology vol. 28 (11) 2001).*
Bogdanowicz et al., "Anti-aging properties of the association of Retinaldehyde, Pretocopheryl glucopyranosyl, Glycylglycine ...," Journal of Investigative Dermatology, Growth Factors, Cell Adhesion and Matrix, vol. 133, Supplemental No. 1, May 2013, p. S150, XP-002715765, Abstract only provided.
Boisnic et al., "Comparative Study of the Anti-Aging Effect of Retinaldehyde Alone or Associated with Pretocopheryl in a Surviving Human Skin Model Submitted to Ultraviolet A and B Irradiation," International Journal of Tissue Reactions, vol. 27, No. 3, 2005, pp. 91-99, XP009173915.
Fisher et al., "Pathophysiology of Premature Skin Aging Induced by Ultraviolet Light," New England Journal of Medicine, vol. 337, No. 20, Nov. 13, 1997, pp. 1419-1428.
French Preliminary Search Report for French Application No. 1355036, dated Oct. 31, 2013.
International Search Report (Forms PCT/ISA/220 and PCT/ISA/210) for International Application No. PCT/EP2014/061488, dated Aug. 8, 2014.
Kaya et al., "Decrease in Epidermal CD44 Expression as a Potential Mechanism for Abnormal Hyaluronate Accumulation in Superficial Dermis in Lichen Sclerosus et Atrophicus," Journal of Investigative Dermatology, vol. 115, No. 6, Dec. 2000, pp. 1054-1058.
Kaya et al., "Selective suppression of CD44 in keratinocytes of mice bearing an antisense CD44 transgene driven by a tissue-specific promoter disrupts hyaluronate metabolism in the skin and impairs keratinocyte proliferation," Genes and Development, vol. 11, No. 8, 1997, pp. 996-1007.
Saurat et al., "Topical Retinaldehyde on Human Skin: Biologic Effects and Tolerance," Journal of Investigative Dermatology, vol. 103, No. 6, Dec. 1994, pp. 770-774.
Sorg et al., "Retinoids in cosmeceuticals," Dermatologic Therapy, vol. 19, No. 5, 2006, pp. 289-296.

(Continued)

*Primary Examiner* — James H Alstrum-Acevedo
*Assistant Examiner* — Tara L Martinez
(74) *Attorney, Agent, or Firm* — Birch, Stewart, Kolasch & Birch LLP (57) ABSTRACT

The invention concerns topical compositions based on retinaldehyde, glycylglycine oleamide and, if necessary, delta-tocopheryl-glucopyranoside, and their use in cosmetology and dermatology to combat skin ageing and more particularly light-induced skin ageing.

22 Claims, 4 Drawing Sheets

(56) References Cited

OTHER PUBLICATIONS

Sorg et al., "Retinol and Retinyl Ester Epidermal Pools Are Not Identically Sensitive to UVB Irradiation and Anti-Oxidant Protective Effect," Dermatology, Clinical and Laboratory Investigations, vol. 199, No. 4, 1999, pp. 302-307.

Tran et al., "Topical Delivery of Retinoids Counteracts the UVB-induced Epidermal Vitamin A Depletion in Hairless Mouse," Photochemistry and Photobiology, vol. 73, No. 4, 2001 (Posted on the website Feb. 2, 2001), pp. 425-431.

* cited by examiner

OGG: Glycylglycine oleamide; Pre-toco: delta-tocopheryl-glucopyranoside; RAL: retinaldehyde.

COSMETIC OR DERMATOLOGICAL COMPOSITIONS COMBINING COSMETIQUES RETINALDEHYDE AND GLYCYLGLYCINE OLEAMIDE AND THE COSMETIC OR DERMATOLOGICAL USES THEREOF

The object of the present invention is topical compositions based on retinaldehyde and glycylglycine oleamide and if necessary delta-tocopheryl-glucopyranoside, their use in cosmetology and dermatology.

DESCRIPTION OF INVENTION

The skin owes its flexibility and its resistance to the different layers of tissues which make it up: The epidermis, the dermis and the hypodermis. The epidermis, the outer layer of the skin is responsible for its imperviousness and its resistance. It essentially consists of keratin, a fibrous protein produced by keratinocytes and of melanin, the main skin pigment made by the melanocytes. Over the years, the renewal of keratinocytes is carried out more slowly and their terminal differentiation is slowed down. Over time, profound changes occur at the dermis. A tissue supporting the skin, it consists of 80% of elastin fibres and of collagen embedded in a gel of glycoproteins. The fibroblasts which are the main cells of the dermis, are specialized in the synthesis of these elastin fibres and of collagen. Between 20 and 80 years old, population of fibroblasts is reduced by half. They ensure the balance between synthesis, maturation and degradation of the elastin fibres and of collagen. Over time, this balance will be moved towards a degradation of these fibres with as results a loss of elasticity and tonicity of the dermis and flaccidity which no longer opposes the effects of contraction of the underlying muscles, leading to the occurrence of wrinkles. The collagen fibres are distributed in all the layers of the dermis, they are capable of binding water and contribute to hydration of the skin. A reduction in collagen and/or a change in its quality lead to the occurrence of deep wrinkles. With ageing, the elastin fibres which give elasticity and solidity to the tissues, become increasingly scarce, the skin becomes thinner and forms wrinkles. The skin continuously has to confront multiple outer aggressions which may accelerate the natural ageing process. It is particularly sensitive to attacks from free radicals generated both by normal operation of our body and by exterior elements, such as pollution, tobacco, and especially solar radiation. These free radicals are responsible for tissue and cell changes which lead to skin ageing.

Vitamin A (retinol) and its natural and synthetic derivatives, collectively designated as retinoids, form a large variety of substances having pronounced effects, notably in embryogenesis, reproduction, vision, growth, inflammation, differentiation, proliferation and apoptosis. The biological effects of retinoids are mediated by their interaction with nuclear receptors of the RAR type (receptor of retinoic acid) and of the RXR type (X receptor of retinoic acid). The known ligand of the RAR receptors is the trans isomer of the acid form of vitamin A.

The skin contains significant amounts of retinoids, as well as the enzymes involved in their metabolism. Retinoids are natural or synthetic derivatives of vitamin A. Like natural retinoids, mention may be made of retinol and all its metabolic derivatives, retinaldehyde, all-trans-retinoic acid, 9-cis-retinoic acid, 13-cis-retinoic acid as well as its esters such as retinyl palmitate. Synthetic retinoids are molecules for which one portion has been modified for the purpose of having compounds having a single effect relative to vitamin A. The main molecules are etretinate, acitretin, tazarotene, adapalene, bexarotene, motretinide.

The human epidermis contains two main forms of vitamin A, retinol and retinylic esters. Vitamin A is stored in the keratinocytes by esterification of retinol into retinylic esters. This step is catalysed by two enzymes, acyl CoA acyltransferase and lecithin retinol acyltransferase. Their expression is modulated by UV radiations and the differentiation condition of the keratinocytes. The hydrolysis of retinylic esters into retinol is catalysed by retinyl ester hydrolase. On the other hand, retinol is a pro-hormone of retinoic acid, it is oxidized into retinaldehyde which itself is oxidized into retinoic acid, a biologically active form of vitamin A. Retinylic esters are considered as the storage form of vitamin A, given that their concentrations in the epidermis, and mainly in the stratum corneum, are higher than in the dermis or further in the blood and they are the precursors of other active forms of vitamin A. The chemical nature of the retinoids, comprising a polyunsaturated lipid chain, as well as their physical properties giving them a maximum of absorption comprised between 320 and 390 nm, makes them capable of interacting with UVs, or with oxygen in order to produce reactive forms of oxygen or free radicals. They may be isomerized by UVs. But in the major number of cases, the retinoids are purely and simply destroyed under the action of UVs. It would seem that retinylic esters are more sensitive than retinol. The epidermis exposed to the sun contains less retinylic esters than unexposed skin, indicating that the UVs induce a deficiency in vitamin A (Sorg et al., Dermatology, 199(4): 302-307, 1999). This and other observations support the hypothesis that depletion of vitamin A induced by the sun is implicated in the pathogenesis of certain skin cancers as well as premature aging (Sorg et al., Dermatol. Ther., 19(5): 289-296, 2006). This depletion may be compensated by external supply of vitamin A.

The topical application of retinoids is known for supplying vitamin A to the skin. Moreover it is known that one of the major secondary effects of retinoids during topical application remains the induced irritation. This effect may be redhibitory to the observance of the treatment.

Topical retinol exerts similar biological effects but less intense than those of topical retinoic acid, with however less irritation, these reactions are mediated by the conversion of retinol into retinoic acid. Retinol, as well as its esters should imperatively be converted into retinoic acid in order to induce biological effects in human keratinocytes. In the same way, retinaldehyde which is converted both into a storage form (retinylic esters) or into an active form (retinoic acid), exerts significant biological activities and is better tolerated than retinoic acid (Saurat et al., J. Invest. Dermatol., 103: 770-774, 1994). It is also a good candidate for supplying vitamin A in the epidermis. It was demonstrated that retinaldehyde exerts a biological activity in the skin by inducing epidermal hyperplasia, as well as a clear increase in the expression of CD44 and of hyaluronate in the follicular and interfollicular epidermis of C57BL/6 and hairless SKH1 mice (hairless mice). These effects were also observed following topical application of retinoic acid and of retinol. However, the expression of CD44 and that of hyaluronate were more strongly increased in mice treated with retinaldehyde. CD44 is a polymorphic transmembrane glycoprotein which has several isoforms generated by alternative splicing and post-translational changes. It was demonstrated that two major functions of CD44 in murine skin are 1) regulation of the keratinocyte proliferation in response to extracellular stimuli and 2) maintaining local homeostasis of hyaluronate (Kaya et al., Genes & Development, 11(8): 996-1007, 1997). A reduction in the expression of epidermal CD44 was also observed in patients suffering from lichen sclerosus, which is potentially responsible for dermal deposition of hyaluronate and of epidermal atrophy in this disease (Kaya et al., J. Invest. Dermatol., 115(6): 1054-1058, 2000).

The application of retinoids is accomplished according to two strategies in dermatology:
  at pharmacological doses in the case of treatment of skin pathologies, the application of retinoic acid (0.025% to 0.1% gels or creams) has as a main indication the treatment of acne. It is also used in the treatment of photo-ageing and of actinic keratoses. Tazarotene is indicated in the treatment of psoriasis (0.05% to 0.1% gels). Motretinide (0.1% cream or lotion) is, as for it, indicated in the treatment of slight acne.
  For cosmetic purposes: retinyl palmitate (0.5% to 5% gels), retinol (0.1% to 0.6%) and retinaldehyde (0.05%) are used for anti-ageing treatments and restorative care.

Solar radiations include visible light, ultraviolets (UV), infrareds and other electromagnetic radiations. In the same way as visible light may be divided into several colours, UVs may be classified in three subdivisions:
  UVAs (315-400 nm) represent the major portion of UVs which reach the surface of the earth. They cause on the skin tan and may damage it in depth because of their facility in penetrating tissues.
  UVBs (280-315 nm) represent a much smaller proportion of rays reaching the ground, but have a significant contribution to consecutive biological effects to solar exposures. They may cause redness, burns, tan, ocular lesions. Their penetration into the skin is lower.
  UVCs (200-280 nm) are practically entirely absorbed by the ozone layer of the atmosphere. They only penetrate the skin very slightly but may cause ocular lesions.

The main effects of UVs on the skin are erythema, photosenescence, skin cancer. After exposure to UVs, there is an increase in the expression of metalloproteinases in the epidermis and the dermis. These enzymes which alter the production of collagen in the dermis contribute to the occurrence of wrinkles. Induction of these enzymes is maintained by repeated exposures (Fisher et al., N. Engl. J. Med., 337: 1419-1428, 1997). There is thickening of the dermis due to the accumulation of elastic material. The production of interleukins by the epidermis, following UV irradiation, contributes to the destruction of the connective tissue. It would seem that the effects observed in the dermis may be ascribed to UVAs, which penetrate as far as it, unlike UVBs. In hairless mice, like in humans, the occurrence of hyperplasia and of wrinkles is observed after long term irradiation with UVBs, and the skin becomes flaccid under the action of UVAs. The observed effects depend on the wavelength of the irradiations. The derm becomes thicker, after irradiation with wavelengths comprised between 295 and 300 nm, the collagen fibres are damaged and there is production of abnormal elastic fibres, this is referred to as elastosis. After 10 weeks of irradiation with UVAs, there are no longer any normal elastic fibres.

Many studies have allowed establishment of a link between chronic solar exposure and predisposition in developing skin cancers. Further, UVs modify certain genes such as p53 responsible for the removal or repair of lesions at the DNA level. UVBs and UVAs do not have the same effect on cell immunity in humans. UVAs are less carcinogenic. UVBs therefore play a dominant role in the carcinogenic effect of solar exposure. The pigmentation is a factor involved in the constitutive sensitivity to UVs. The UVAs absorbed by melanin of the melanocytes would be at the origin of skin cancers. In fact, UVAs are responsible for the initiation of the melanoma, but UVBs are also responsible for its development until metastasis.

The main indication for retinaldehyde and retinoic acid is the treatment of heliodermy, which corresponds to skin ageing, often premature, generated by chronic and/or prolonged exposures to the sun. The lesions are directly dependent on the received dose.

The glycylglycine oleamide of formula:

is a lipo-peptide or acyl-peptide from the condensation of oleic acid and the glycylglycine dipeptide.

Glycylglycine oleamide is known for its surfactant properties in liquid detergent compositions (U.S. Pat. No. 4,732, 690 and JP-59 84 994). The object of patent EP-1 061 897 is the use of glycylglycine oleamide for making a composition intended to counter glycation and elastosis of the protein fibres of the connective tissue and more generally by stimulating cell metabolism.

Alpha-tocopherol or vitamin E is found in the natural condition, in many plants, usually with other compounds such as beta-tocopherol, gamma-tocopherol or delta-tocopherol. Alpha-tocopherol is essentially used for combating deficiencies in vitamin E, or as a nutritional factor, notably for combating muscle degeneration. It is also used as an antioxidant, but at very specific doses. Cosmetological compositions containing these tocopherols are already commercially available. However, it has been demonstrated that under mild oxidation conditions, direct application of these antioxidants on the skin causes pro-inflammatory effects which are the consequence of over activity at the concentrations commonly used. Thus, many structural changes in these tocopherols have given the possibility of limiting the secondary effects, allowing them to be used in treating or preventing other diseases or disorders of the skin. Thus, WO 98/51679 discloses tocopherol esters in cosmetic or pharmaceutical compositions. It is described in the international application that these tocopherols esters are anti-radical, anti-inflammatory, promoting keratinocyte differentiation, improving skin hydration and smoothness of the grain of the skin, for preventing or treating skin aging effects, with skin-lightening activity or anesthetic action on nerve endings. Patent EP 1062223 describes precursors of actives in cosmetology or dermatology, more particularly in the treatment of skin diseases (atopic dermatitis, acne, psoriasis). The principle of the invention is related to the use of glucocerebrosidase, which is a lysosomal enzyme present in all cells and therefore naturally present in the skin. Glucocerebrosidase hydrolyzes the active precursor, thereby releasing the biologically active substance. By this means, the secondary effects are reduced, or even suppressed. This patent also discloses the use of carbohydrate precursors of delta-tocopherol and more particularly physicochemical and biological characteristics of delta-tocopherol-glucopyranoside. Enzymatic hydrolysis of delta-tocopherol-glucopyranoside by glucocerebrosidase slowly releases delta-tocopherol, with lower kinetics than a reference derivative (4-methylumbelliferyl glucopyranoside). This slow release gives the possibility of avoiding overconcentration of the delta-tocopherol active and therefore any inflammatory effect during the application of the product. Thus, the slow release of the active ensures better bioavailability of the latter in the skin medium and therefore more efficient protection. In particular in EP 1062223, the very low activity of gluco-conjugates is disclosed as compared with that of free actives: in particular, delta-tocopherol-glucopyranoside has a low antioxidant potential as compared with that of delta-tocopherol.

The studies conducted by the applicant gave the possibility of revealing synergy on the metabolism of retinoids in keratinocytes with the combination of retinaldehyde and of glycylglycine oleamide.

Surprisingly, delta-tocopherol-glucopyranoside combined with retinaldehyde and glycylglycine oleamide has dermatological activity on the whole of the dermis, revealing a very pronounced effect for combating skin ageing and more particularly against photo-induced skin ageing. Thus, the combination of the three actives has a very wide spectrum of action on many genes, the expression of which is modified during photo-induced ageing.

The object of the invention relates to a cosmetic or dermatological composition comprising as a main ingredient retinaldehyde and glycylglycine oleamide.

The object of the invention also relates to a cosmetic or dermatological composition comprising as an active ingredient retinaldehyde and glycylglycine oleamide, and at least one cosmetically or dermatologically acceptable carrier.

According to another embodiment, the composition comprises as an active ingredient, retinaldehyde, glycylglycine oleamide and delta-tocopheryl-glucopyranoside, and at least one cosmetically or dermatologically acceptable carrier.

According to a preferred embodiment, the excipient appears in a form intended for topical application. The object of the invention is most particularly intended for topical application on skin areas considered as fragile, such as for example the face, the neck, the contour of the eyes and of the lips.

By "carrier" is meant any adjuvant or excipient allowing the making, the preservation and the administration of the cosmetic or dermatological composition. Any carrier acceptable from the cosmetic or dermatological point of view, for example selected from among the excipients commonly used in galenic mixing, may be used in the composition according to the invention.

Advantageously, the composition according to the invention contains from 0.01 to 1% by weight of retinaldehyde, preferably from 0.015 to 0.1% by weight of retinaldehyde based on the total weight of the composition.

According to a preferred embodiment of the invention, the composition contains 0.015% by weight of retinaldehyde based on the total weight of the composition.

According to another preferred embodiment of the invention, the composition contains 0.05% by weight of retinaldehyde based on the total weight of the composition.

According to still another preferred embodiment of the invention, the composition contains 0.1% by weight of retinaldehyde based on the total weight of the composition.

Advantageously, the composition according to the invention contains from 0.0001 to 20% by weight of glycylglycine oleamide, preferably from 0.001 to 10% by weight of glycylglycine oleamide, preferably from 0.01 to 1% by weight of the glycylglycine oleamide, more advantageously from 0.05 to 0.5% by weight of glycylglycine oleamide, based on the total weight of the composition.

According to a preferred embodiment of the invention, the composition contains 0.1% by weight glycylglycine oleamide based on the total weight of the composition.

Advantageously, the composition according to the invention contains from 0.001 to 10% by weight of delta-tocopheryl-glucopyranoside, preferably from 0.01 to 5% by weight of delta-tocopheryl-glucopyranoside, preferably from 0.05 to 0.5% by weight of delta-tocopheryl-glucopyranoside, and still more advantageously from 0.05 to 0.15% by weight of delta-tocopheryl-glucopyranoside based on the total weight of the composition.

According to a preferred embodiment of the invention, the composition contains from 0.05 to 0.1% by weight of delta-tocopheryl-glucopyranoside based on the total weight of the composition.

According to a preferred embodiment of the invention, the composition according to the invention contains from 0.01 to 0.1% of retinaldehyde, 0.1% of glycylglycine oleamide and from 0.05 to 0.1% of delta-tocopheryl-glucopyranoside, based on the total weight of the composition.

The composition according to the invention may appear as an oil-in-water emulsion (O/W) or water-in-oil (W/O) emulsion. It may also appear as spherules like liposomes, nanocapsules or nanospheres.

The fatty phases which may be used in the invention are:
solid or pasty fatty phases such as bees waxes, candelilla waxes, carnauba waxes, petroleum wax (or microcrystalline wax), paraffin; and mixtures thereof;
oils of animal and/or plant origin; and mixtures thereof;
hydrocarbon oils of synthetic origin, with more than 8 carbon atoms, which may be linear, or branched, saturated or unsaturated, such as hydrogenated polyisobutylene (parleam oil), paraffin oil (or Vaseline, or paraffinum liquidum), isoparaffins, limonene, squalene, polyisobutene or isooctane; and mixtures thereof;
oils formed with higher fatty acids, notably $C_{10}$-$C_{22}$ fatty acids, such as myristic acid, palmitic acid, stearic acid, behenic acid, oleic acid, linoleic acid, linolenic acid or isostearic acid;
oils formed with higher fatty alcohols, notably $C_{10}$-$C_{22}$ alcohols, such as oleic alcohol, linoleic alcohol or linolenic alcohol, isostearic alcohol or octyl dodecanol; and mixtures thereof;
oils formed with linear or branched, saturated or unsaturated esters, of formula RCOOR' wherein R represents the remainder of a higher fatty acid including from 7 to 19 carbon atoms and R' represents a hydrocarbon chain including from 3 to 20 carbon atoms, in particular $C_{12}$-$C_{36}$ esters, such as isopropyl myristate, isopropyl palmitate, butyl stearate, hexyl laurate, diisopropyl adipate, isononyl isononanoate, 2-ethyl-hexyl palmitate, 2-hexyl-decyl laurate, 2-octyldecyl palmitate, 2-octyl-dodecyl myristate or lactate, di(2-ethyl-hexyl) succinate, diisostearyl malate, isostearyl hydroxystearate, ethylhexyl hydroxystearate, cetearyl ethylhexanoate; isostearyl isostearate; and mixtures thereof;

oils formed with monoglycerides of $C_1$-$C_{30}$ carboxylic acids, diglycerides of $C_1$-$C_{30}$ carboxylic acid, triglycerides of $C_1$-$C_{30}$ carboxylic acids, such as caprylic and capric acid mono-, di- or tri-glyceride, palmitic acid mono-, di- and tri-glyceride, linoleic acid mono-, di- and tri-glyceride, stearic acid mono-, di- and tri-glyceride, isostearic acid mono-, di- and tri-glyceride, behenic acid mono-, di- and tri-glyceride, oleic acid mono-, di- and tri-glyceride, myristic acid mono-, di- and tri-glyceride, linolenic acid mono-, di- and tri-glyceride; and mixtures thereof;

non-volatile silicone oils such as non-volatile polydimethylsiloxanes (PDMS); modified polysiloxanes; aminated silicones, or with hydroxyl group, or fluorinated; dimethicones; trimethicones; and mixtures thereof. Preferably, the dimethicones which may be used within the scope of the present invention are accessible under the trade names VICASIL® (General Electric Company), DOW CORNING 200® (Dow Corning Corporation, DC200), DOW CORNING 225®, or any other fatty phase known to one skilled in the art.

The composition may also comprise agents for conditioning the skin. Examples of conditioning agents of the skin may comprise but are not limited to anionic, cationic, non-ionic emulsifiers such as sodium lauryl sulfate, sodium dioctyl sulfosuccinate, sodium stearate, sorbitan ester, ethoxylated fatty acids, ethoxylated fatty alcohols, trideceth-9 and PEG-5 ethylhexanoate, and any emulsifier and conditioning agent known to one skilled in the art.

For the compositions according to the invention having an alcohol-aqueous or alcoholic base, the use of any mono-alcohol is suitable.

The composition may further comprise a polyol miscible with water at room temperature (25° C.) notably selected from among polyols notably having from 2 to 20 carbon atoms, preferably having from 2 to 10 carbon atoms, and preferentially having from 2 to 6 carbon atoms, such as glycerol, glycol derivatives such as propylene glycol, butylene glycol, pentylene glycol, hexylene glycol, dipropylene glycol, diethylene glycol; glycol ethers such as mono-, di- or tri-propylene glycol ($C_1$-$C_4$) alkyl ethers, mono-, di- or tri-ethylene glycol ($C_1$-$C_4$) alkyl ethers; and mixtures thereof.

The composition may further comprise antimicrobial agents such as preservatives or antifungal agents selected from alcohols, which may contain one or several aromatic substituents, for example phenoxyethanol like 2-phenoxyethanol, 1-phenoxy-2-propanol, benzyl alcohol, 2-hydroxy-biphenyl, imidazolidinyl urea, diazolidinyl urea, sodium hydroxymethylglycinate, halogenated derivatives such as iodopropynyl butylcarbamate, 2-bromo-2-nitropropan-1,3-diol, 2,4,4'-trichloro-2'-hydroxydiphenylether (triclosan), 3,4,4'-trichlorocarbanilide (triclocarban), chlorbutanulum, 2,4-dichlorobenzyl alcohol, N-4-chlorophenyl-N'-3,4-dichlorophenyl urea, 1,2-dibromo-2,4-dicyanobutane, chloroxylenol, ketoconazole, oxiconazole, butoconazole, clotrimazole, econazole, enilconazole, fenticonazole, miconazole, sulconazole, tioconazole, fluconazole, itraconazole, terconazole, actives containing one or several cationic nitrogen atoms such as cetyltrimethylammonium chloride, cetylpyridinium chloride, benzethonium chloride, diisobutylethoxyethyl-dimethylbenzylammonium chloride, diisobutyl-phenoxy-ethoxyethyl-dimethylbenzylammonium chloride, N-alkyl-N,N-dimethylbenzylammonium chloride, bromide saccharinate, trimethylammonium chloride, sodium aluminium chlorohydroxylacetate, tricetylmethylammonium chloride, diaminoalkylamide, organic acids and their salts, such as citric acid, unsaturated antimicrobial agents such as farnesol, terbinafine or naftifine, heterocyclic aromatic agents such as bifonazole, cloconazole, isoconazole, and any other antimicrobial or antifungal agent known to one skilled in the art and mixtures thereof.

The composition may also comprise thickeners or agents for modifying rheology, such as for example hydrophobically modified ethoxylated non-ionic urethanes, thickening polycarboxylic acids such as the copolymer of acrylates/steareth-20 methacrylate, carbomers, copolymers of acrylates and acrylates and cross-linked $C_{10}$-$C_{30}$ alkyl acrylates; and mixtures thereof.

The composition may also comprise acids and bases allowing adjustment of the pH zone of said composition. The bases may be mineral (soda, potash, ammonia) or organic such as mono-, di- or tri-ethanolamine, an aminomethylpropanediol, N-methyl-glucamine, basic amino acids like arginine and lysine; and mixtures thereof.

The compositions may further comprise one or several other ingredients such as pH buffers, vitamins, fragrances, and any other useful compound well known to one skilled in the art.

The composition according to the invention may be conditioned as an ointment, a spray, a lotion, a gel, a foam, a dispersion, a serum, a mask, a body milk or cream.

The compositions according to the invention may be used in cosmetology and in dermatology for preventing or improving wrinkled skins and give the possibility of maintaining the firmness and the humidity of the skin.

The compositions according to the invention may be used in topical preparations, in the field of dermatology or cosmetology, with the purpose of preventing and/or reducing wrinkles, combating either photo-induced skin ageing or not, of re-initiating epidermal and dermal cell activity, firming the skin, increasing its elasticity, increasing the physiological reserves of the skin in vitamin A.

The invention also relates to the cosmetic use of the composition according to the invention for combating ageing of the skin, and more particularly against photo-induced skin ageing.

The invention also relates to the cosmetic use of the composition according to the invention for increasing the physiological reserves of the skin in vitamin A.

The invention also relates to a cosmetic method for combating photo-induced skin ageing comprising the application on the skin of the composition according to the invention.

The invention also relates to a cosmetic method for increasing the physiological reserves of the skin in vitamin A comprising the application on the skin of the composition according to the invention.

The invention also relates to a composition according to the invention for its use as a dermatological drug for treating skin affections in connection with a deficiency of the physiological reserves of the skin in vitamin A.

The present invention is illustrated in a non-limiting way by the following examples.

EXAMPLE 1

Preventing depletion induced by UV radiations by a pre-treatment with topical retinoids (Tran et al., Photochem. Photobiol. 73(4): 425-431, 2001).

The study is carried out in hairless mice. The retinoids are applied topically for 7 days at 0.05%, and then UVB radiation (1 J/cm$^2$) is produced. The epidermal retinoids are assayed 24 h after the radiation.

Figure 1:
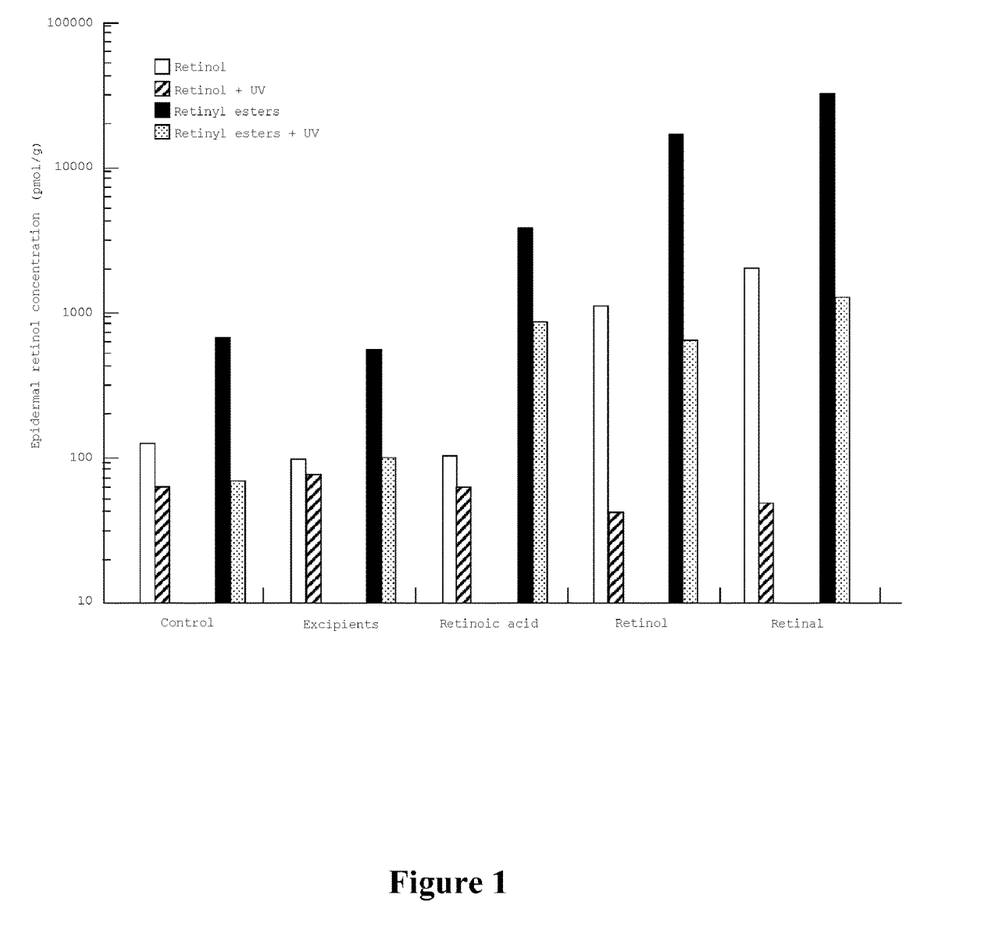
FIG. 1 is a graph which shows prevention of UV-induced depletion by a pre-treatment with topical retinoids, as provided in Example 1.

The results are illustrated in FIG. 1 which has as a title: prevention of UV-induced depletion by a pre-treatment with topical retinoids.

Retinaldehyde and retinol prevent photo-induced depletion of epidermal retinylic esters by loading the epidermis with retinoids. Retinoic acid thus prevents the photo-induced depletion of retinoids, without providing any substrate, but by inducing lecithin retinol acyltransferase.

Conclusion: it is the retinaldehyde which has the best profile in this study of photo-induced depletion of retinoids.

EXAMPLE 2

Modulation of Retinylic Esters Induced by Retinoids in Keratinocytes

The study was carried out on keratinocytes A431 in a culture. Indeed, in these cells, no endogenous retinoid was measured. A retinoid has to be applied beforehand in order to measure cell retinoids. The retinoids were measured by HPLC. The incubation in the presence of various agents or combination of agents dissolved in 1% of ethanol in the culture medium, was carried out for 24 to 72 h.

The production of retinoids in the keratinocytes is shown in the table below. These are averaged values expressed in pmol/mg of protein.

TABLE 1

| Treatment | Retinol | Retinylic esters | Total |
|---|---|---|---|
| Ethanol (1%) | <10 | <10 | <10 |
| OA (15 µM) | <10 | <10 | <10 |
| GG (15 µM) | <10 | <10 | <10 |
| OGG (15 µM) | <10 | <10 | <10 |
| ROL-Pal (15 µM) | 389 | 178 | 567 |
| RAL (2 µM) | 865 | 280 | 1145 |
| RAL + OA | 673 | 304 | 977 |
| RAL + GG | 676 | 238 | 914 |
| RAL + OGG | 945 | 484 | 1429 |

OA: oleic acid; GG: glycylglycine; OGG: glycylglycine oleamide; ROL-Pal: retinyl palmitate; RAL: retinaldehyde.

This experiment gives the possibility of establishing that retinaldehyde induces a series of retinylic esters. These retinylic esters induced by retinaldehyde are significantly increased by glycylglycine oleamide, exhibiting real synergy through this association. The retinyl palmitate is incorporated into the cells, and then hydrolyzed into retinol, and then the formed retinol is partly esterified, finally giving less cell retinoids than retinaldehyde.

Figure 2:
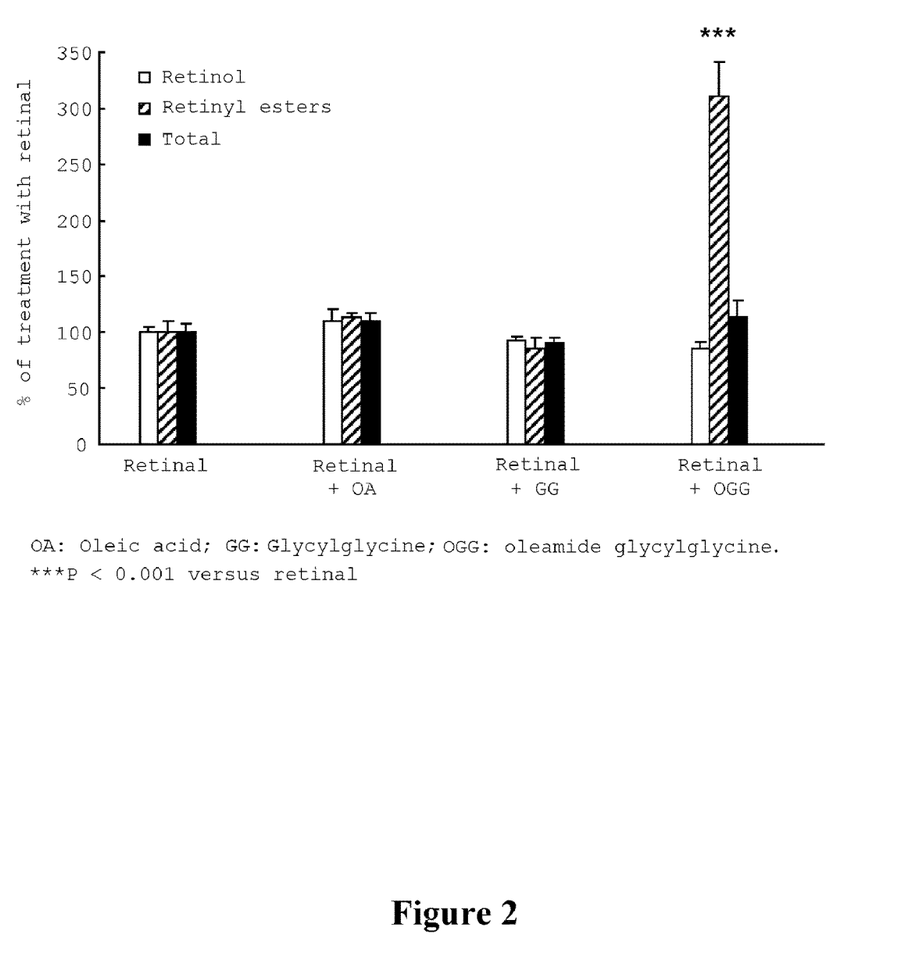
FIG. 2 is a graph showing the synergy induced by the association of retinaldehyde and of glycylglycine oleamide on the modulation of the retinylic esters induced in the keratinocytes after incubation, as provided in Example 2.

FIG. 2 shows the synergy induced by the association of retinaldehyde and of glycylglycine oleamide on the modulation of the retinylic esters induced in the keratinocytes after 48 h of incubation. The values are expressed in percentage of the treatment with retinaldehyde.

EXAMPLE 3

Effect of the Combination of Retinaldehyde and of Glycylglycine Oleamide and of Delta-Tocopheryl-Glucopyranoside on Human Dermal Fibroblasts Irradiated with UVAs.

The goal of this study is to evaluate the protective properties of these three actives before irradiation of the fibroblasts.

The study was carried out on normal human dermal fibroblasts, sown in 12-well plates and cultivated in a culture medium for 24 hours.

For seeking a protective effect, the culture medium was replaced with a medium either containing or not (control) the mixture of the products to be tested, and the cells were incubated for 24 hours. At the end of the pre-incubation, the medium was replaced with an irradiation medium in the absence of the compounds and then the cells were either irradiated or not (non-irradiated control) by UVAs (20 J/cm$^2$). At the end of the irradiation, the medium was replaced with a test medium and the cells were incubated for 48 hours. All the experimental conditions were produced in n=3. At the end of the experiment, the RNAs were extracted and the expression of 64 genes was measured by RT-PCR.

The mixture consists in:
- 1 µM of retinaldehyde
- 1 µM of glycylglycine oleamide
- 10 µM of delta-tocopheryl-glucopyranoside.

Figure 3:
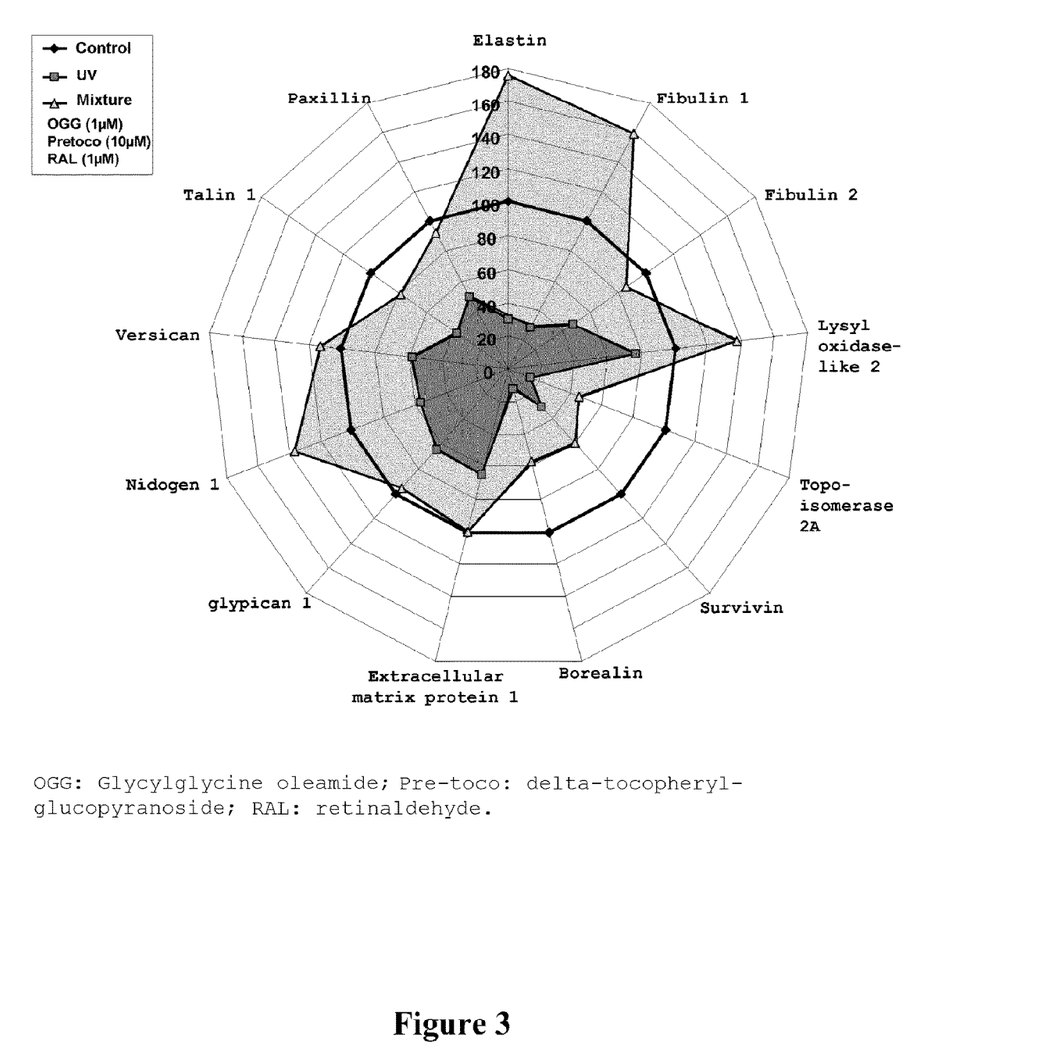
FIG. 3 is a graph showing the effect of the combination of retinaldehyde and of glycylglycine oleamide and of delta-tocopheryl-glucopyranoside on human dermal fibroblasts irradiated with UVAs, as provided in Example 3.

Irradiation by UVAs of human dermal fibroblasts clearly inhibited the expression of many genes involved in the assembling of the extracellular matrix as well as the expression of certain components of this matrix (FIG. 3). In parallel, clear stimulation of the MMP1 and MMP3 markers, involved in the degradation of the extracellular matrix in the regulation of the cell cycle was inhibited. On the 64 tested genes, 25 were regulated by UVs. These results were expected and gave the possibility of validating the experiment.

In the presence of the mixture of the three actives, as shown in FIG. 3, a substantial protective effect is observed on 13 genes, the expression of which was modified by the irradiation.

Surprisingly, the mixture of these three actives gives the possibility of observing a protective effect both on genes involved in the elastic network of the skin (like elastin, fibulin 1), in the interactions between the cells and the extracellular matrix (like for example paxillin, versican) but also in the protection of the nucleus of the cells (survivin, borealin).

FIG. 3 gives the possibility of viewing that the mixture of these three actives restores the expression of the genes affected by the irradiation but also keying a potentialization of the expression of 4 genes, relatively to the control conditions (elastin, fibulin, lysyl oxidase-like 2 and nidogen 1).

Thus, the mixture of these three actives not only allows rectification of the alterations produced by the irradiation, but the dermal protective effect is so important, notably on the genes involved in the elasticity of the skin where a real reorganization of the skin elastic network is observed and that the mixture of these three actives is highly effective for combating skin ageing.

EXAMPLE 4

Effect of the Combination of Glycylglycine Oleamide, of Retinaldehyde and of Delta-Tocopheryl-Glucopyranoside on the Elastic Network of Human Skin Irradiated with UVAs.

The study was carried out on human skin explants sown in 6-well plates and cultivated in a culture medium for 48 hours. The skin was either irradiated or not (non-irradiated control) with UVAs (12 J/cm$^2$). For seeking a protective effect, a formula either containing or not (placebo control) the mixture of glycylglycine oleamide at 0.1%, of retinaldehyde at 0.05%, and of delta-tocopheryl-glucopyranoside at 0.05% was applied to the surface of the skin (10 mg/cm$^2$) until the end of the irradiation. After 24 hours of incubation, the same amount of protective formula was again applied on the skin. The experiment was extended to 24 hours at the end of which the skin was frozen and treated for viewing the elastic network of the skin dermis by immunohistochemistry in confocal fluorescence microscopy. The expression of fibrillin and of elastin was analyzed by means of specific antibodies.

Figure 4:
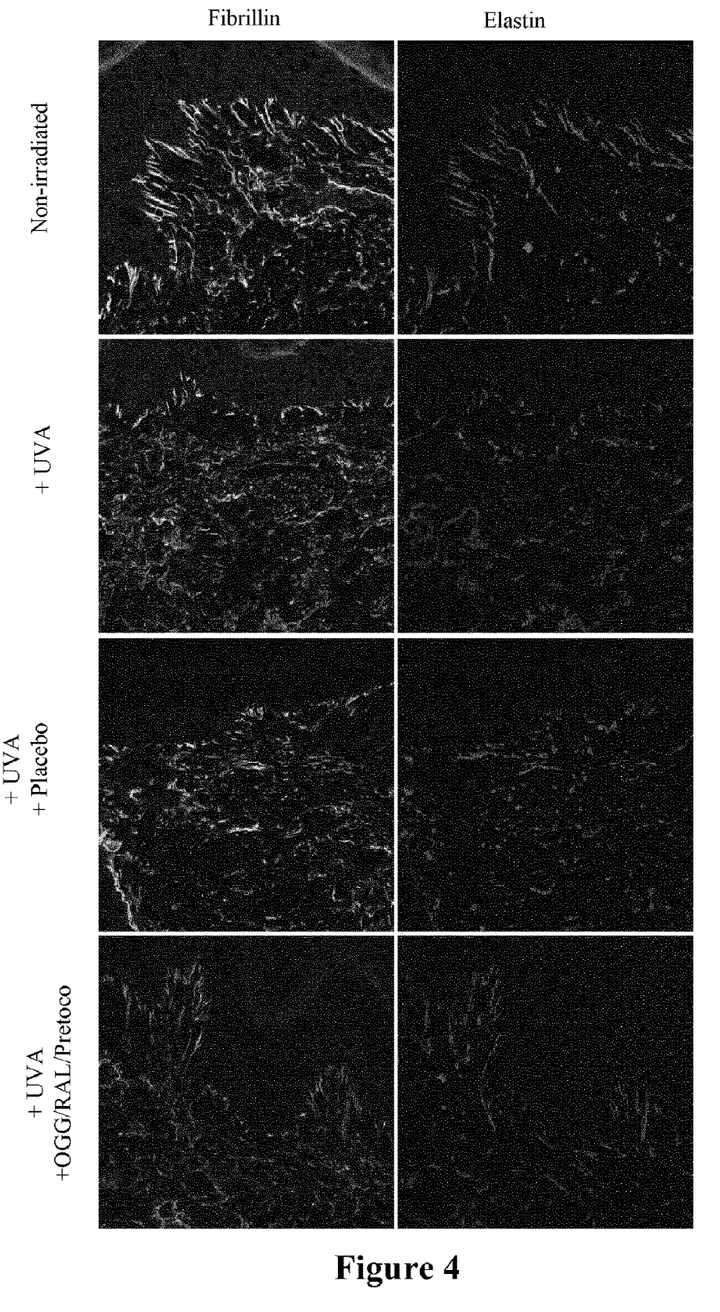
FIG. 4 are pictures showing the effect of the combination of glycylglycine oleamide, of retinaldehyde and of delta-tocopheryl- glucopyranoside on the elastic network of human skin irradiated with UVAs, as provided in Example 4.

The results are illustrated in FIG. 4 concerning topical application of the glycylglycine oleamide, retinaldehyde and delta-tocopheryl-glucopyranoside mixture, protecting skin against alterations of the elastic fibres induced by UVA irradiation. Indeed, irradiation by UVA of skin explants strongly damage the expression of fibrillin and of elastin in the dermis and caused a substantial disorganization of the network of elastic fibers with many breakages. The placebo control did not protect the skin and exhibited an elastic network similar to the UVA-irradiated skin. On the other hand, the formula containing the three actives allows restoration of the structure of the elastic fibers affected by the UVAs and protection of the elasticity of the skin. The structure of the elastic network of the irradiated skin and treated with the mixture of actives is identical with that of a non-irradiated control skin.

The combination of glycylglycine oleamide, retinaldehyde and delta-tocopheryl-glucopyranoside therefore gives the possibility of reorganizing the elastic skin tissue and of protecting the skin against alterations generated by UVAs. Thus, the mixture of the three actives preserves the skin elasticity and effectively acts against photo-ageing of the skin.

The whole of the results proves that the combination of retinaldehyde and of glycylglycine oleamide by its synergy will give the possibility of durably increasing the physiological reserves of the skin in vitamin A. The combination of retinaldehyde, glycylglycine oleamide and delta-tocopheryl-glucopyranoside will give the possibility of effectively combating skin ageing by synergistically acting at the dermis on a multitude of targets.

EXAMPLE 5: CREAM

|  | % by weight |
|---|---|
| Glycylglycine oleamide | 0.1 |
| Retinaldehyde | 0.1 |
| Delta-tocopheryl-glucopyranoside | 0.1 |
| Glycerine | 6 |
| Disodium EDTA | 0.1 |
| Phenoxyethanol | 0.35 |
| C$_{10}$-C$_{30}$ alkylcrosspolymer | 0.4 |
| Glyceryl stearate & PEG-100 stearate | 4 |
| Cetyl alcohol | 1 |
| Caprylic/Capric triglycerides | 10 |
| Dimethicone | 4 |
| Dicaprylyl carbonate | 4 |
| Water | QSP 100% |

The invention claimed is:

1. A method for combating ageing of the skin by increasing the physiological stores of vitamin A in the skin, said method comprising:
applying on the skin a therapeutically effective amount of a cosmetic or dermatological composition comprising as an active ingredient retinaldehyde and glycylglycine oleamide and at least one cosmetically or dermatologically acceptable carrier.

2. A cosmetic method for increasing the physiological store of vitamin A in the skin, said method comprising:
applying on the skin a therapeutically effective amount of a cosmetic or dermatological composition comprising as an active ingredient retinaldehyde and glycylglycine oleamide and at least one cosmetically or dermatologically acceptable carrier.

3. A method for treating skin disorders in a patient having a deficiency in the physiological reserves of vitamin A in the skin, said method comprising:
administering a therapeutically effective amount of a cosmetic or dermatological composition comprising as an active ingredient retinaldehyde and glycylglycine oleamide and at least one cosmetically or dermatologically acceptable carrier.

4. The method according to claim 1, said composition further comprising delta-tocopheryl-glucopyranoside.

5. The method according to claim 1, wherein said composition contains 0.01 to 1% by weight of retinaldehyde based on the total weight of the composition.

6. The method according to claim 1, wherein said composition contains 0.0001 to 20% by weight of glycylglycine oleamide based on the total weight of the composition.

7. The method according to claim 1, wherein the composition further comprises 0.001 to 10% of delta-tocopheryl-glucopyranoside based on the total weight of the composition.

8. The method according to claim 1, wherein the composition contains 0.01 to 0.1% of retinaldehyde, 0.1% of glycylglycine oleamide and further comprises 0.05 to 0.1% of delta-tocopheryl-glucopyranoside, based on the total weight of the composition.

9. The method according to claim 1, said composition further comprising an excipient in a form intended for topical application.

10. The method according to claim 1, wherein the ageing includes photo-induced skin ageing.

11. The method according to claim 2, said composition further comprising delta-tocopheryl-glucopyranoside.

12. The method according to claim 2, wherein said composition contains 0.01 to 1% by weight of retinaldehyde based on the total weight of the composition.

13. The method according to claim 2, wherein said composition contains 0.0001 to 20% by weight of glycylglycine oleamide based on the total weight of the composition.

14. The method according to claim 2, wherein the composition further comprises 0.001 to 10% of delta-tocopheryl-glucopyranoside based on the total weight of the composition.

15. The method according to claim 2, wherein the composition contains 0.01 to 0.1% of retinaldehyde, 0.1% of glycylglycine oleamide and further comprises 0.05 to 0.1% of delta-tocopheryl-glucopyranoside, based on the total weight of the composition.

16. The method according to claim 2, said composition further comprising an excipient in a form intended for topical application.

17. The method according to claim 3, said composition further comprising delta-tocopheryl-glucopyranoside.

18. The method according to claim 3, wherein said composition contains 0.01 to 1% by weight of retinaldehyde based on the total weight of the composition.

19. The method according to claim 3, wherein said composition contains 0.0001 to 20% by weight of glycylglycine oleamide based on the total weight of the composition.

20. The method according to claim 3, wherein the composition further comprises 0.001 to 10% of delta-tocopheryl-glucopyranoside based on the total weight of the composition.

21. The method according to claim 3, wherein the composition contains 0.01 to 0.1% of retinaldehyde, 0.1% of glycylglycine oleamide and further comprises 0.05 to 0.1% of delta-tocopheryl-glucopyranoside, based on the total weight of the composition.

22. The method according to claim 3, said composition further comprising an excipient in a form intended for topical application.

* * * * *